(12) United States Patent
Kuai et al.

(10) Patent No.: US 7,273,707 B2
(45) Date of Patent: Sep. 25, 2007

(54) METHOD OF IDENTIFYING A MODULATOR OF A LTβR COMPLEX SIGNALING PATHWAY

(75) Inventors: Jun Kuai, Lexington, MA (US); Joseph L. Wooters, Brighton, MA (US); Elliott Nickbarg, Belmont, MA (US); Yongchang Qiu, Arlington, MA (US); Lih-Ling Lin, Concord, MA (US)

(73) Assignee: Wyeth, Madison, NJ (US)

( * ) Notice: Subject to any disclaimer, the term of this patent is extended or adjusted under 35 U.S.C. 154(b) by 317 days.

(21) Appl. No.: 10/361,270

(22) Filed: Feb. 10, 2003

(65) Prior Publication Data

US 2004/0038299 A1    Feb. 26, 2004

Related U.S. Application Data

(60) Provisional application No. 60/355,183, filed on Feb. 8, 2002.

(51) Int. Cl.
*G01N 33/53* (2006.01)
*C07K 1/00* (2006.01)

(52) U.S. Cl. ............... 435/7.1; 435/7.21; 530/350; 530/351

(58) Field of Classification Search ............ 530/350, 530/351; 424/7.1, 7.2
See application file for complete search history.

(56) References Cited

U.S. PATENT DOCUMENTS 5,925,351 A * 7/1999 Browning et al. ........ 424/143.1
6,235,878 B1   5/2001 Nishi et al. .............. 530/350

OTHER PUBLICATIONS

Zhai et al., Journal of Clinical Investigation, vol. 102, No. 6, pp. 1142-1151, Sep. 1998.*
Nguyen et al., Immunity, vol. 11, pp. 379-389, Sep. 1999.*
Ye et al., Molecular Cell, vol. 4, pp. 321-330, Sep. 1999.*
McCarthy et al., The Journal of Biological Chemistry, vol. 273, No. 27, Jul. 3, 1998.*
Holcik et al., Apoptosis, vol. 6, No. 4, pp. 253-261, 2001.*
Amente et al., FEBS Letters, vol. 579, Ni.3, pp. 683-689, Jan. 2005.*
Browning, et al., "Signaling Through the Lymphotoxin β Receptor Induces the Death of some Adenocarcinoma Tumor Lines", *J. Exp. Med.*, 183(3):867-878 (1996).
Chai, et al., "Structural and Biochemical Basis of Apoptotic Activation bySmac/DIABLO" *Nature*, 406:855-862 (2000).
Du, et al., "Smac, a Mitochondrial Protein that Promotes Cytochrome c-Dependent Caspase Activation by Eliminating IAP Inhibition", *Cell*, 102(1):33-42 (2000).
Force, et al., "Dominant Negative Mutants of TRAF3 Reveal an Important Role for the Coiled Domains in Cell Death Signaling by the Lymphotoxin-β Receptor", *J. Biol. Cem.*, 272:30835-30840 (1997).
International Search Report, mailing date: Oct. 9, 2003.
Kuai, et al., "Endogenous Association of TRAF2, TRAF3, cIAP1, and Smac with Lymphotoxin β Receptor Reveals a Novel Mechanism of Apoptosis", *J. Biol. Chem.*, 278(16): 14363-14369 (2003).
Wajant, et al., "TNF Receptor Associated Factors in Cytokine Signaling", *Cytokine & Growth Factor Reviews*, 10(1):15-26 (1999).
Wu, et al., "Structural Basis of IAP Recognition by Smac/DIABLO", *Nature*, 408: 1008-1012 (2000).
Yoshikawa, et al., "IFN-γ Induces the Apoptosis of WEHI 279 and Normal Pre-B Cell Lines by Expressing Direct Inhibitor of Apoptosis Protein Binding Protein with Low pI", *Immunol.*, 167(5):2487-2495 (2001).

* cited by examiner

*Primary Examiner*—Eileen B. O'Hara
(74) *Attorney, Agent, or Firm*—Ivor R. Elrifi, Esq.; David E. Johnson, Esq.; Mintz Levin

(57) ABSTRACT

The invention relates to compositions and methods comprising lymphotoxin-beta receptor (LTβR) modulators, which activate or inhibit LTβR signaling. LTβR modulators are useful for treating lymphocyte mediated immunological diseases and cancer, and more particularly, for regulating mitochondrial-mediated apoptosis. This invention relates to soluble forms of the LTβR complex proteins that act as LTβR activating or inhibiting agents. This invention also relates to the use of soluble molecules, directed against either the LTβR, its ligands, LIGHT and LTβ1α2, or its intracellular binding partners, that function to regulate LTβR signaling. A novel screening method for selecting soluble receptors, antibodies and other agents that modulate LTβR signaling is provided.

27 Claims, 3 Drawing Sheets

METHOD OF IDENTIFYING A MODULATOR OF A LTβR COMPLEX SIGNALING PATHWAY

RELATED APPLICATIONS

This application claims priority to U.S. Ser. No. 60/355,183, filed Feb. 8, 2002. The contents of this application are incorporated herein by reference in their entirety.

FIELD OF THE INVENTION

This invention relates to compositions and methods for identifying modulators of immune responses and more particularly to compositions and methods for identifying modulators of immune responses using members of the lymphotoxin-beta receptor (LTβR) complex.

BACKGROUND OF THE INVENTION

Lymphotoxin-β receptor (LTβR), a non-death domain containing receptor of the tumor necrosis factor receptor (TNFR) family, is reported to play an important role in organogenesis of secondary lymphoid tissues. Two types of ligands for LTβR have been described. These have been identified as the heterotrimer LTα1β2 and the homotrimer LIGHT.

LTβR signaling is believed to be mediated by signaling molecules recruited to the intracellular domain of the receptor upon binding of a ligand. Like other members in the TNFR family, multiple signaling pathways are activated by the ligand-LTβR complex, including apoptosis, activation of NFκB and JNK pathway.

Apoptosis, or programmed cell death, is a normal cell suicide function. There are two major signaling pathways of apoptosis, the death receptor pathway and the mitochondrial pathway. Signals from both pathways lead to the activation of a common cascade of caspases, which subsequently cleave a large number of cellular proteins resulting in cell death. Most of the death domain-containing receptors induce apoptosis by recruitment of FADD and activation of caspase 8. In contrast, LTβR lacks a death domain sequence and thus does not interact with FADD. Moreover, the cell death induced by LTβR has a characteristic of a slow apoptosis process and is dependent on interferon γ. Therefore, LTβR-induced apoptosis is thought to be activated by mechanism that is distinct from a death domain-dependent mechanism.

SUMMARY OF THE INVENTION

The invention is based in part on the discovery of polypeptides associated with the lymphotoxin β receptor (LTβR) complex signaling pathway. Included in these newly identified components of the LTβR are the polypeptides Smac, cIAP1, and TRAF2, and enhancer of rudimentary (ERH). Also identified in the complex is TRAF3, which has previously been shown to associate with the LTβR complex. Smac has been reported to be implicated in a mitochondrial mediated apoptosis pathway.

Accordingly, in one aspect, the invention provides a purified complex comprising a (LTβR) polypeptide and a Smac polypeptide. In a preferred embodiment, the LTβR polypeptide is bound to a LTβR ligand. The LTβR ligand can be either a LIGHT polypeptide or an Ltα1β2 polypeptide. The complex can also include a cIAP1 polypeptide, a TRAF3 polypeptide, and a TRAF2 polypeptide. The amino acid sequences from these polypeptides can be from a mammal, e.g., a human, non-human primate, rodent, or another eukaryote such as *Drosophila melanogaster*. In a preferred embodiment, these polypeptides have human amino acid sequences.

In another aspect, the invention includes a purified complex comprising a LTβR polypeptide, a LTβR ligand, a TRAF2 polypeptide, a TRAF3 polypeptide, a cIAP1 polypeptide, and a Smac polypeptide.

In another aspect, the invention includes a method of identifying a modulator of a Tumor Necrosis Factor Receptor (TNFR) family member signaling pathway by contacting a cell expressing a TNFR family member with a test agent and determining whether the test agent modulates mitochondrial-mediated apoptosis in the cell. In a preferred embodiment, TNFR family member does not contain a death domain. In another embodiment, the TNFR family member is a LTβR polypeptide. In another preferred embodiment, the LTβR complex comprises LβTR, TRAF3, TRAF2, cIAP1, and Smac polypeptides. The test agent can either inhibit or activate LTβR signaling activity. In a preferred embodiment, the modulator is identified by determining activity or expression of a Smac polypeptide in the cell or by determining the interaction of cIAP1 polypeptide or a TRAF2 polypeptide with a Smac polypeptide.

The invention additionally provides a method of identifying a modulator of a lymphotoxin beta receptor (LTβR) complex signaling pathway by contacting a cell expressing an LTβR polypeptide with a test agent and determining whether the test agent modulates activity or expression of a Smac polypeptide in the cell.

In another aspect, the invention includes a method of identifying a modulator of a LTβR complex signaling pathway by contacting a cell expressing an LTβR with a test agent and determining whether the test agent modulates activity or expression of a cIAP1 polypeptide in the cell.

In another aspect, the invention provides a method of identifying a modulator of a LTβR complex signaling pathway by contacting a cell expressing an LTβR with a test agent and determining whether the test agent modulates activity or expression of a TRAF2 polypeptide in the cell.

In another aspect, the invention provides a method for identifying a modulator of an LTβR activity by contacting a test agent with a TRAF2, cIAP1, or Smac polypeptide and determining whether the test agent modulates activity of the polypeptide, thereby identifying a modulator of LTβR activity. In a preferred embodiment, the method further comprises determining whether the test agent binds directly to the polypeptide and whether the test agent affects activity or expression of the polypeptide.

In another aspect, the invention includes a method for identifying a modulator of a LTβR complex signaling pathway by contacting a Smac polypeptide with a test agent; and determining whether the test agent inhibits activity of the Smac polypeptide, thereby identifying an inhibitor of an LTβR complex signaling pathway.

In a another aspect, the invention includes a method for identifying an agent for treating or preventing an immune disorder by contacting a cell expressing a Tumor Necrosis Factor Receptor (TNFR) TNFR family member with a test agent and determining whether the test agent modulates mitochondrial-mediated apoptosis in the cell, thereby identifying an agent for treating or preventing an immune disorder. In a preferred embodiment, the TNFR family member does not contain a death domain and is a lymphotoxin β receptor (LTβR) polypeptide. This method can be used to identify an agent useful for treating an immune disorder selected from but not limited to, rheumatoid arthritis, systemic lupus erythematosus, Goodpasture's syndrome, Grave's disease, Hashimoto's thyroiditis, pemphigus vulgaris, myasthenia gravis, scleroderma, autoimmune hemolytic anemia, autoimmune thrombocytopenic purpura, polymyositis and dermatomyositis, pernicious anemia, Sjögren's syndrome, ankylosing spondylitis, vasculitis or Type I diabetes mellitus.

In a further aspect, the invention provides for a method for identifying an agent for treating or preventing cancer contacting a cell expressing a TNFR family member with a test agent and determining whether the test agent modulates mitochondrial-mediated apoptosis in the cell, thereby identifying an agent for treating or preventing cancer.

Also within the invention are modulators identified by the above-referenced screening methods, and methods of using these inhibitors to modulate an immune response.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1A:
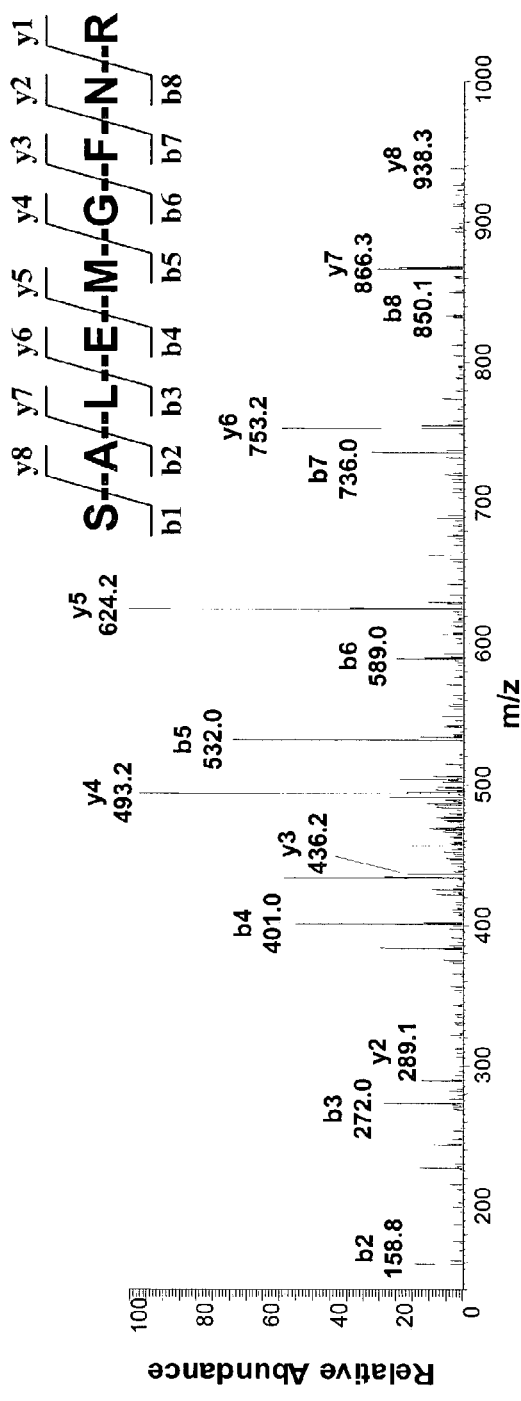
FIG. 1A is a representative fragment ion spectra of peptides identified as being derived from cIAP1.

The invention provides methods for identifying lymphotoxin-beta receptor (LTβR) modulators, which can activate or inhibit LTβR signaling. The LTβR, or members of the complex, including those newly identified herein, can be used as an agent, or serve as a target for agents, that can be used to inhibit or stimulate LTβR mediated inhibition of mitochondrial apoptosis, for example to block abnormal cell growth or to extend cell growth in culture. The modulators identified herein can be used to treat a variety of indications, including immune conditions and cancer. A preferred indication is rheumatoid arthritis The following terms are intended to have the following general meanings as they are used herein:

The term "apoptosis" refers to a process of programmed cell death.

The term "cytokine" refers to a molecule which mediates interactions between cells. A "lymphokine" is a cytokine released by lymphocytes.

The term "LTβR modulator" refers to any agent which can activate or inhibit ligand binding to LTβR, cell surface LTβR clustering or LTβR signaling, or which can influence how the LTβR signal is interpreted within the cell. Examples of LTβR activating agents include, IFN-α, IFN-γ, TNF, soluble anti-LTβR antibodies, cross-linked anti-LTβR antibodies and multivalent anti-LTβR antibodies, soluble LIGHT polypeptide or soluble Ltα1β2 polypeptide.

The term "LTβR signaling" refers to molecular reactions associated with the LTβR pathway and subsequent molecular reactions that result therefrom.

The term "substantially pure" polypeptide means a polypeptide or polypeptide complex separated from components that naturally accompany it. Typically, the polypeptide or polypeptide complex is substantially pure when is at least 60%, by weight, free from the proteins and naturally-occurring organic molecules with which it is naturally associated. Preferably, the purity of the preparation is at least 75%, more preferably at least 90%, and most preferably at least 99%, by weight.

Lymphotoxin-β Receptor Associated Polypeptides

The invention includes polypeptides that have been identified as components of the Lymphotoxin-β Receptor complex. These newly identified members of the LTbR complex include TRAF2, cIAP1, and Smac.

Smac is a mitochondrial protein but is released to the cytosol concurrent with the release of cytochrome c during apoptosis. The cytosolic Smac is then recruited to the receptor through the interaction with cIAP1 and relieves the inhibition of apoptosis by cIAP1. cIAP1 has been reported to inhibit apoptosis by inhibiting the activity of caspases.

The amino acid sequences for these polypeptides are provided below. For TRAF2, and Smac nucleic acid sequences are additionally provided.

The amino acid sequence of the TRAF2 polypeptide is provided below:

(SEQ ID NO:1)
MAAASVTPPGSLELLQPGFSKTLLGTKLEAKYLCSACRNVLRRPFQAQCGHRYCSFCLASILSSGPQNCA

ACVEEGIYEEGISILESSSAFPDNAARREVESLPAVCPSDGCTWKGTLKEYESCHEGRCPLMLTECPACK

GLVRLGEKERHLEHECPERSLSCRHCRAPCCGADVKAHHEVCPKFPLTCDGCGKKKIPREKFQDHVKTCG

KCRVPCRFHAIGCLETVEGEKQQEHEVQWLREHLAMLLSSVLEAKPLLGDQSHAGSELLQRCESLEKKTA

TFENIVCVLNREVERVAMTAEACSRQHRLDQDKIEALSSKVQQLERSIGLKDLAMADLEQKVRPFQAQCG

HRYCSFCLASILRKLQEAVAGRIPAIFSPAFYTSRYGYKMCLRIYLNGDGTGRGTHLSLFFVVMKGPNDA

LLRWPFNQKVTLMLLDQNNREHVIDAFRPDVTSSSFQRPVNDMNIASGCPLFCPVSKMEAKNSYVRDDAI

FIKAIVDLTGL

A nucleic acid sequence encoding the disclosed TRAF2 amino acid sequence is provided below:

(SEQ ID NO:2)
```
atggctgcagctagcgtgaccccccctggctccctggagttgctacagcccggcttctccaagaccctcctggggacc
aagctggaagccaagtacctgtgctccgcctgcagaaacgtcctccgcaggcccttccaggcgcagtgtggccaccgg
tactgctccttctgcctggccagcatcctcagctctgggcctcagaactgtgctgcctgtgttcacgagggcatatat
gaagaaggcatttctattttagaaagcagttcggccttcccagataatgctgcccgcagggaggtggagagcctgccg
gccgtctgtcccagtgatggatgcacctggaaggggaccctgaaagaatacgagagctgccacgaaggccgctgcccg
ctcatgctgaccgaatgtcccgcgtgtaaaggcctggtccgccttggtgaaaaggagcgccacctggagcacgagtgc
ccggagagaagcctgagctgccggcattgccgggcaccctgccgcggagcagacgtgaaggcgcaccacgaggtctgc
cccaagttccccttaacttgtgacggctgcggcaagaagaagatcccccgggagaagtttcaggaccacgtcaagact
tgtggcaagtgtcgagtcccttgcagattccacgccatcggctgcctcgagacggtagagggtgagaaacagcaggag
cacgaggtgcagtggctgcgggagcacctggccatgctactgagctcggtgctggaggcaaagcccctcttgggagac
cagagccacgcggggtcagagctcctgcagaggtgcgagagcctggagaagaagacggccacttttgagaacattgtc
tgcgtcctgaaccggggaggtggagagggtggccatgactgccgaggcctgcagccggcagcaccggctggaccaagac
aagattgaagccctgagtagcaaggtgcagcagctggagaggagcattggcctcaaggacctggcgatggctgacttg
gagcagaaggtcaggccttccaggcgcagtgtggccaccggtactgctccttctgcctggccagcatcctcaggaag
ctccaggaagctgtggctggccgcatacccgccatcttctcccagccttctacaccagcaggtacggctacaagatg
tgtctgcgtatctacctgaacggcgacggcaccgggcgaggaacacacctgtccctcttctttgtggtgatgaaggc
ccgaatgacgccctgctgcggtggcccttcaaccagaaggtgaccttaatgctgctcgaccagaataaccgggagcac
gtgattgacgccttcaggcccgacgtgacttcatcctcttttcagaggccagtcaacgacatgaacatcgcaagcggc
tgcccctcttctgcccgtctccaagatggaggcaaagaattcctacgtgcgggacgatgccatcttcatcaaggcc
attgtggacctgacagggctctaa
```

The amino acid sequence of the IAP1 polypeptide is shown below:

(SEQ ID NO:3)
```
MHKTASQRLFPGPSYQNIKSIMEDSTILSDWTNSNKQKMKYDFSCELYRMSTYSTFPAGVPVSERSLARA
GFYYTGVNDKVKCFCCGLMLDNWKLGDSPIQKHKQLYPSCSFIQNLVSASLGSTSKNTSPMRNSFAHSLS
PTLEHSSLFSGSYSSLSPNPLNSRAVEDISSSRTNPYSYAMSTEEARFLTYHMWPLTFLSPSELARAGFY
YIGPGDRVACFACGGKLSNWEPKDDAMSEHRRHFPNCPFLENSLETLRFSISNLSMQTHAARMRTFMYWP
SSVPVQPEQLASAGFYYVGPNDDVKCFCCDGGLRCWESGDDPNVEHAXWFPRCEFLIRMKGQEFVDEIQG
RYPHLLEQLLSTSDTTGEENADPPIIHFGPGESSSEDAVMMNTPVVKSALEMGFNRDLVKQTVQSKILTT
GENYKTVNDIVSALLNAEDEKREEEKEKQAEEMASDDLSLIRKNRMALFQQLTCVLPILDNLLKANVINK
QEHDIIKQKTQIPLQARELIDTILVKGNAAANIFKNCLKEIDSTLYKNLFVDKNMKYIPTEDVSGLSLEE
QLRRLQEERTCKVCMDKEVSVVFIPCGHLVVCQECAPSLRKCPICRGIIKGTVRTFLS
```

The amino acid sequence of the Smac polypeptide is shown below:

(SEQ ID NO:4)
```
MAALKSWLSRSVTSFFRYRQCLCVPVVANFKKRCFSELIRPWHRTVTIGFGVTLCAVPIAQKSEPHSLSS
EALMRRAVSLVTDSTSTFLSQTTYALIEAITEYTKAVYTLTSLYRQYTSLLGKMNSEEEDEVWQVIIGAR
```

-continued

AEMTSKHQEYLKLETTWMTAVGLSEMAAEAAYQTGADQASITARNHIQLVKLQVEEVHQLSRKAETKLAE

AQIEELRQKTQEEGEERAESEQEAYLRED

A nucleic acid sequence encoding the disclosed Smac polypeptide is shown below:

(SEQ ID NO:5)
Atggcggctctgaagagttggctgtcgcgcagcgtaacttcattcttcaggtacagacagtgtttgtgtgttcctgtt gtggctaactttaagaagcggtgtttctcagaattgataagaccatggcacagaactgtgacgattggctttggagta accctgtgtgcggttcctattgcacagaaatcagagcctcattcccttagtagtgaagcattgatgaggagagcagtg tctttggtaacagatagcacctctacctttctctctcagaccacatatgcgttgattgaagctattactgaatatact aaggctgtttataccttaacttctctttaccgacaatatacaagtttacttgggaaaatgaattcagaggaggaagat gaagtgtggcaggtgatcataggagccagagctgagatgacttcaaaacaccaagagtacttgaagctggaaaccact tggatgactgcagttggtctttcagagatggcagcagaagctgcatatcaaactggcgcagatcaggcctctataacc gccaggaatcacattcagctggtgaaactgcaggtggaagaggtgcaccagctctcccggaaagcagaaaccaagctg gcagaagcacagatagaagagctccgtcagaaaacacaggaggaaggggaggagcgggctgagtcggagcaggaggcc tacctgcgtgaggattga The amino acid sequence of an enhancer of rudimentary homologue (ERH) polypeptide found is shown below:

(SEQ ID NO:6)
MSHTILLVQPTKRPEGRTYADYESVNECMEGVCKMYEEHLKRNNPNSPSITYDISQLFDFIDDLADLSCL

VYRADTQTYQPYNKDWIKEKIYVLLRRQAQQAGK

The nucleotide sequence encoding the disclosed ERH polypeptide is shown below:

(SEQ ID NO:7)
atgtctcacaccatttgctggtacagcctaccaagaggccagaaggcagaacttatgctgactacgaatctgtgaat gaatgcatggaaggtgtttgtaaaatgtatgaagaacatctgaaaagaatgaatcccaacagtccctctatcacatat gacatcagtcagttgtttgatttcatcgatgatctggcagacctcagctgcctggtttaccgagctgatacccagaca taccagccttataacaaagactggattaaagagaagatctacgtgctccttcgtcggcaggcccaacaggctgggaaa taa Protein complexes of the invention including two or more of the above-disclosed polypeptides along with, in various embodiments, a LTβR receptor, a LTβR ligand (such as LIGHT), and TRAF3 polypeptide. A preferred LTβR complex includes a LTβR receptor, LIGHT, TRAF2, cIAP1, ERH, and TRAF3. A complex can be obtained, for example, by extraction from a natural source, by expression of recombinant nucleic acids encoding the members of the complex, by expression of a polypeptide fragment fusion proteins, or by chemical synthesis. A chemically synthesized polypeptide or a polypeptide produced in a cellular system different from the cell from which it naturally occurs is, by definition, substantially free from components that naturally accompany it. Accordingly, substantially pure polypeptides include those derived from eukaryotic organisms but synthesized in recombinant cells of *E. coli* or other prokaryotes. Purity can be measured by any appropriate methods, e.g., column chromatography, polyacrylamide gel electrophoresis, or by HPLC analysis.

Modulation of LTβR Signaling

The invention additionally provides methods of identifying agents that modulate lymphoxin β receptor signaling, including methods that rely on the presence and or activity of one or more of the LTβR complex polypeptides disclosed above.

LTβR complexes are members of the Tumor Necrosis Factor (TNF)-receptors. TNF-related cytokines have emerged as a large family of pleiotropic mediators of host defense and immune regulation. Members of this family exist in membrane-bound forms which act locally through cell-cell contact, or as secreted proteins which can act on distant targets. A parallel family of TNF-related receptors react with these cytokines and trigger a variety of pathways including cell death, cell proliferation, tissue differentiation and pro-inflammatory responses.

In non-tumorigenic cells, TNF and many of the TNF family ligand-receptor interactions influence immune system development and responses to various immune challenges. The LTβR, a member of the TNF family of receptors, specifically binds to surface LT ligands. Signaling by LTβR may play a role in peripheral lymphoid organ development and in humoral immune responses. LTβR signaling, like TNF-R signaling, also has anti-proliferative effects and can be cytotoxic to tumor cells. LTβR mRNAs are found in human spleen, thymus and other major organs LTβR expression patterns show that LTβR is lacking in peripheral blood T cells and T cell lines. Accordingly, agents identified in the screening methods described herein can be used to treat a variety of indications.

In one aspect, agents that can modulate LTβR signaling are selected based on their ability by block mitochondrial-mediated apoptosis. A modulator of a LTβR signaling pathway is identified by contacting a cell expressing a LTβR with a test agent and determining whether the test agent modulates mitochondrial-mediated apoptosis in the cell. Alternatively, an agent can be selected by determining whether it modulates activity or expression of a cIAP1, TRAF2, or Smac polypeptide in the cell.

In general, any compound can be used as a test agent. Suitable test agents include, e.g., proteins, nucleic acids, carbohydrates, or small molecules. For example, the test agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des* 12:145).

Examples of methods for the synthesis of molecular libraries can be found in the art, for example in: DeWitt et al. (1993) *Proc Natl Acad Sci U.S.A.* 90:6909; Erb et al. (1994) *Proc Natl Acad Sci U.S.A.* 91:11422; Zuckermann et al. (1994) *J Med Chem* 37:2678; Cho et al. (1993) *Science* 261:1303; Carrell et al. (1994) *Angew Chem Int Ed Engl* 33:2059; Carell et al. (1994) *Angew Chem Int Ed Engl* 33:2061; and Gallop et al. (1994) *J Med Chem* 37:1233.

Libraries of compounds may be presented in solution (e.g., Houghten (1992) *BioTechniques* 13:412-421), or on beads (Lam (1991) *Nature* 354:82-84), on chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci U.S.A.* 89:1865-1869) or on phage (Scott and Smith (1990) *Science* 249:386-390; Devlin (1990) *Science* 249:404-406; Cwirla et al. (1990) *Proc Natl Acad Sci U.S.A.* 87:6378-6382; Felici (1991) *J Mol Biol* 222:301-310; Ladner above.).

In general, assays recognized in the art can be used to assess mitochondrial-mediated apoptosis. Such asssays are described in, e.g., U.S. Pat. No. 5,935,937. One example is the following: (1) tumor cells such as HT29 or MCF-7 cells are cultured for three to four days in a series of tissue culture wells containing media and at least one LTβR activating agent in the presence or absence of serial dilutions of the agent being tested; (2) a vital dye stain which measures mitochondrial function such as MTT is added to the tumor cell mixture and reacted for several hours; (3) the optical density of the mixture in each well is quantified. The optical density is proportional to the number of tumor cells remaining in the presence of the LTβR activating agent and the test LTβR blocking agent in each well.

The invention can additionally use known or putative LTβR modulating activating agents. Agents that induce LTβR signaling (such as activating soluble LTβR fragments or anti-LTβR monoclonal antibodies, and modified forms thereof) can be selected based on their ability, alone or in combination with other agents, for example the interaction of Smac with cIAP1, to potentiate tumor cell cytotoxicity through mitochondrial-mediated apoptosis using the tumor cell assay described above.

Another method for selecting an LTβR modulation agent is to monitor the ability of the putative agent to directly interfere with LTβR-ligand binding. Any of a number of assays that measure the strength of ligand-receptor binding can be used to perform competition assays with putative LTβR blocking agents. The strength of the binding between a receptor and ligand can be measured using an enzyme-linked immunoadsorption assay (ELISA) or a radio-immunoassay (RIA). Specific binding may also be measured by fluorescently labelling antibody-antigen complexes and performing fluorescence-activated cell sorting (FACS) analysis, or by performing other such immunodetection methods, all of which are techniques well known in the art.

The ligand-receptor binding interaction may also be measured with the BIACORE™ instrument (Pharmacia Biosensor) which exploits plasmon resonance detection (Zhou et al., Biochemistry, 32, pp. 8193-98 (1993); Faegerstram and O'Shannessy, "Surface plasmon resonance detection in affinity technologies", in Handbook of Affinity Chromatography, pp. 229-52, Marcel Dekker, Inc., New York (1993)).

With any of these or other techniques for measuring receptor-ligand interactions, one can evaluate the ability of a LTβR blocking agent, alone or in combination with other agents, to inhibit binding of surface or soluble LT ligands to surface or soluble LTβR molecules. Such assays may also be used to test LTβR blocking agents or derivatives of such agents (e.g. fusions, chimeras, mutants, and chemically altered forms), alone or in combination, to optimize the ability of that altered agent to block LTβR activation.

The invention will be further illustrated in the following non-limiting examples.

EXAMPLE 1

Materials and Methods

The materials and methods used in the examples below included the following.

Cell Culture, Antibodies and Reagents

U937, HEK293 and MCF7 cells were obtained from American Type Culture Collection (ATCC) and cultured in RPMI 1640 (Gibco BRL), DME (Gibco BRL) and EMEM (ATCC) with 0.01% insulin, respectively. All media were supplemented with 10% FBS. TRAF2 and TRAF3 antibodies were purchased from Santa Cruz Biotechnology. cIAP1 antibody was obtained from R&D Systems. Anti-Flag (M2) antibody and affinity beads were obtained from Sigma. HA antibody (3F10) was purchased from Roche Molecular Chemicals. Smac antibodies were purchased from Alexis Biochemicals and Cell Signaling Technology. All chemical reagents otherwise specified were purchased from Sigma.

Plasmid constructions

N-terminal FLAG-tagged full length LTβR in pFLAG-CMV2 vector (Eastman Kodak, Co.) was a kind gift from Dr. Shie-Liang Hsieh (see also Wu et al., J. Biol. Chem. 274:11868-73, 199). The full-length and Δ76 deletion mutant of Smac with a C-terminal HA-tag were amplified by PCR reaction from a human ovary cDNA library. The PCR fragments were then cloned into pcDNA3.1 (+) at NdeI and XhoI sites.

Purification of Endogenous LIGHT-Receptor Complex $1\times10^{10}$ U937 cells were washed twice with warm PBS (37° C.) and resuspended at a concentration of $1\times10^7$ cells/ml. Cells were either treated or left untreated with 20 ng/ml of Flag-LIGHT (Alexis) for 10 min at 37° C. Cells were then lysed in 50 ml of lysis buffer (20 mM Tris.HCl, pH 7.2, 150 mM NaCl, 1% Triton X-100, 1 mM EDTA, 30 mM NaF, 1 mM NaVO$_4$ and protease inhibitor cocktails (Roche)), and gently rocked at 4° C. for 30 min. Cell debris was removed by centrifugation twice at 10,000 g for 30 min. Lysate was preclarified by incubation with Gamma Binding beads (Pharmacia) for 1 hour. The resulting lysate was applied twice to a mini-column (BioRad) of 0.2 ml M2-affinity beads (Sigma). The beads were washed twice with high salt (1M NaCl) lysis buffer, three times more with lysis buffer and then transferred into an eppendorf tube. The immuno-complex was first eluted with Flag peptide (Sigma) at a concentration of 2 mg/ml. The residual binding proteins were then further eluted with 8M Urea. One half of the peptide-eluted proteins or ⅒ of the 8M Urea-eluted proteins were separated on the 4-12% SDS-PAGE gel and transferred to nitrocellulose membrane for Western blotting using TRAF3 antibody. These samples were also separated on the 4-12% SDS-PAGE gel and visualized by silver staining.

Mass Spectrometry and Protein Identification

Protein bands of interest were manually excised from the gel, reduced and alkylated with iodoacetamide, and then digested in situ with trypsin using an automated digestion robot (ABIMED, Germany) as described by Houthaeve et al., J. Protein Chemistry 16:343-48, 1997. The peptide digests were then sequenced using a high-throughput tandem mass spectrometer (ThermoQuest LCQ-DECA, San Jose Calif.) equipped with a micro-electrospray reversed phase liquid chromatography interface. Data were acquired in automated MS/MS mode using the data acquisition software provided with the LCQ to detect and sequence each peptide as it eluted from the column. The dynamic exclusion and isotope exclusion functions were employed to increase the number of peptide ions that were analyzed. During the LS-MS/MS run, typically >1000 fragmentation spectra were collected from each sample and matched against the nonredundant databases (NCBI) using the Sequest software package (ThermoQuest).

Immunoprecipitation and Western Analysis

For immunoprecipitation, $1\times10_8$ U937 cells were treated with FLAG-LIGHT at 20 ng/ml for different time or left untreated. Cells were then harvested and lysed in 4 ml of lysis buffer (see above). Cell debris was removed by centrifugation at 14,000 xg for 10 min and resulting lysate was pre-cleared with Gamma Binding beads (Pharmacia Biotech) for 1 hour at 4° C. Then 20 μl of M2 beads were added to cell lysate and incubated at 4° C. for 3 hours. After binding, beads were washed five times with lysis buffer. Immune complexes bound to the beads were eluted with sample buffer, resolve on 4-12% SDS-PAGE gels, transferred to PVDF membrane and probed with TRAF2, TRAF3 or cIAP1 antibody. Signals were detected with HRP-conjugated secondary antibody and ECL detection kits (Amersham Pharmacia Biotech). For immunoprecipitation in HEK 293 cells, 4 μg of pFlag-CMV2-LTβR, pcDNA3-Smac-HA or pcDNA3-Δ76Smac-HA were transfected into cells on a 100 mm dish using Fugene 6 (Roche Molecular Biochemicals) according to the manufacture's instruction. Forty-eight hours after transfection, cells were collected with cell lifters and lysed in 0.5 ml of lysis buffer. Immunoprecipitation was performed in the same fashion as in U937 cells, with either M2 beads for LTβR or with HA monoclonal antibody for Smac or Δ76 Smac. The presence of Smac, LTβR, TRAF2 and cIAP1 in the immune complex were then analyzed by Western blots.

Apoptosis Assay

MCF7 cells ($5\times10^5$ cells/well) were seeded on cover slides in 6-well plates one day before transfection. Cells in each well were transfected with 1 μg of pcDNA3 vector, pcDNA3-Smac-HA or pcDNA3-Δ76Smac-HA expression constructs together with pEMC-βGal using Fugene 6 (Roche Molecular Chemicals). Twenty-four hours after transfection, cells were treated with PBS (control), LIGHT (20 ng/ml) or LTα1β2 (20 ng/ml) for 6 hours, then fixed and stained with X-gal (Sigma). Apoptosis was assessed by morphological analysis and expressed as a percentage of apoptotic (round and detached) cells in the total of transfected blue cells.

EXAMPLE 2

Identification of Polypeptides in LTβR Complexes

LIGHT binds to both LTβR and TR2/ HVEM. In U937 cells, LTβR is constitutively expressed while the expression of TR2/ HVEM is induced by differentiating agents. This phenomeonon was exploited to form a specific ligand-LTβR complex. Undifferentiated U937 cells were treated with Flag-tagged LIGHT for 10 minutes to form a LIGHT-LTβR complex. Endogenous receptor complex was affinity-purified with anti-Flag antibody (M2)-conjugated beads and then eluted with Flag peptide. The eluted proteins were resolved on 4-12% SDS-PAGE gels and visualized by silver staining.

Approximately eight protein bands were found to be present only in the LIGHT-treated sample but not in the control. TRAF3 was detecteed in the LIGHT-treated sample using a polyclonal antibody against TRAF3.

In order to identify the additional proteins in this complex, eight bands, which were assigned numbers 1-8, were excised from the gel and analyzed by liquid chromatography electrospray ionization mass spectrometry (LC-ESI-MS). As expected, LIGHT was detected in band 6 (see also Table 1). Several peptides derived from the polypeptide TRAF2 were detected in band 3. Proteins in other bands either could not be determined due to the poor quality of the spectrum or later turned out to be non-specific binding proteins, such as Hsp 90 at band 1 and actin at band 4.

Peptides corresponding to TRAF3 at expected position of band 3 could not be detected, nor could peptides corresponding to receptor polypdpides. One possibility was that the amount of TRAF3 and receptors, if any, was below the detection limit of mass spectrometry. As indicated by the Western blot of TRAF3, Flag peptides only eluted one tenth of the total TRAF3 protein on the beads. This low efficiency was probably due to the multimeric and high affinity interactions between antibody and ligand-receptor complex.

To increase the recovery of proteins from the beads, the beads were treated with 8M Urea. Samples were then resolved on SDS-PAGE gels and bands at expected position of TRAF3 were excised and analyzed by mass spectrometry. Three peptides from TRAF3 (Table 1) were detected in the LIGHT-treated sample. These peptides were absent in the sample without LIGHT treatment.

TABLE 1

List of proteins identified in LIGHT-LTβR complex.

| Proteins | Bands* | Peptides detected | |
|---|---|---|---|
| LIGHT | F6/U6 | AGYYYIYSK | (SEQ ID NO:34) |
| | | ASTITHGLYK | (SEQ ID NO:35) |
| | | SYHDGALVVTK | (SEQ ID NO:8) |
| LTβR | U2 | EYYEPQHR | (SEQ ID NO:9) |
| | | DQEKEYYEPQHR | (SEQ ID NO:10) |
| | | NQFITHD | (SEQ ID NO:11) |
| TRAF3 | U2 | YGCVFQGTNQQIK | (SEQ ID NO:12) |
| | | NTGLLESQLSR | (SEQ ID NO:13) |
| | | TLSLYSQPFYTGYFGYK | (SEQ ID NO:14) |
| TRAF2 | F3/U3 | YLCSACR | (SEQ ID NO:15) |
| | | RPFQAQCGHR | (SEQ ID NO:16) |
| | | CPLMLTECPACK | (SEQ ID NO:17) |
| | | FPLTCDGCGKK | (SEQ ID NO:18) |
| | | FHAIGCLETVEGEK | (SEQ ID NO:19) |
| | | VAMTAEACSR | (SEQ ID NO:20) |
| | | VQQLER | (SEQ ID NO:21) |
| | | DLAMADLEQK | (SEQ ID NO:22) |
| | | RPFQAQCGHR | (SEQ ID NO:23) |
| | | IPAIFSPAFYTSR | (SEQ ID NO:24) |
| | | IYLNGDGTGR | (SEQ ID NO:25) |
| | | WPFNQK | (SEQ ID NO:26) |
| | | NSYVRDDAIFIK | (SEQ ID NO:27) |
| cIAP1 | U2 | AVEDISSSR | (SEQ ID NO:28) |
| | | AGFYYIGPGDR | (SEQ ID NO:29) |
| | | VACFACGGK | (SEQ ID NO:30) |
| | | SALEMGFNR | (SEQ ID NO:31) |
| Smac | U6 | AVYTLTSLYR | (SEQ ID NO:32) |
| | | LAEAQIEELR | (SEQ ID NO:33) |

Figure 1B:
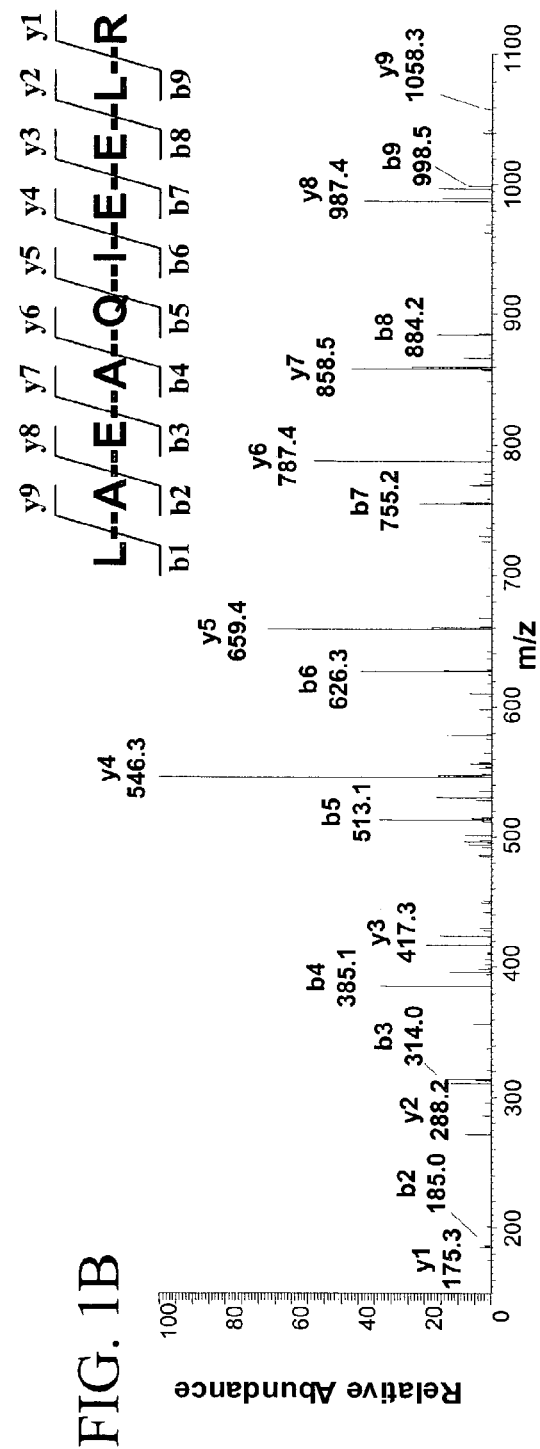
FIG. 1B is a representative fragment ion spectra of peptides identified as being derived from SMAC.

Proteins listed in table were only detected in LIGHT-treated samples but not in control samples.
*F stands for bands in FLAG-eluted sample and U stands for bands in 8M Urea-eluted sample.
Numbers correspond to those indicated in FIG. 1.

All the bands in both LIGHT-treated and control samples were then treated with 8M urea, even though 8M Urea also eluted proteins non-specifically bound to the beads, resulting in an indistinguishable pattern between LIGHT-treated and control samples on SDS-PAGE gels. After protein identification, non-specific binding proteins in the control sample were subtracted from those in the LIGHT-treated sample to yield proteins that specifically bind to the LIGHT-receptor complex. Table 1 summarizes the peptides detected and their assigned proteins. A total of five sproteins were identified, including the four listed above and ERH.

As expected, LTβR was detected as the receptor in the complex (Table 1). The detection of LIGHT and LTβR in the complex further confirmed the successful isolation of LIGHT-LTβR complex. TRAF2 and TRAF3 were also detected (Table 1). In addition, four peptides derived from cIAP1 at the position of band 2 and two peptides derived from Smac at the position of band 6 were detected (Table 1). FIGS. 2A and 2B show two representative mass spectra of cIAP1 and SMAC-derived peptides, respectively.

No TRAF4, TRAF5 or NIK polypeptides were detected by either mass spectrometry or Western blot analysis even though their roles have been suggested in the LTβR signaling. This could be due to the low abundance of the proteins and the high complexity of the samples.

To confirm the association of these proteins with the LIGHT-LTβR complex, U937 cells were treated with Flag-LIGHT for various amounts of time. Cells were then immunoprecipitated with Flag antibody, followed by Western blot analysis using antibody against TRAF2, TRAF3 or cIAP1.

The recruitment of endogenous TRAF2, TRAF3 and cIAP1 to LIGHT-LTβR complex was found to be time-dependent. Recruitment of cIAP1 was gradually increased within 15 minutes. A similar pattern was observed for TRAF3. Recruitment of TRAF2 appeared to be more rapid and appeared to peak between 5 and 10 minutes. The kinetics of recruitment suggests that TRAF2 is recruited to the receptor prior to TRAF3 and cIAP1. The direct interaction of TRAF3 with the intracellular domain of LTβR has been demonstrated using purified proteins (Force et al., J. Biol. Chem. 272:30835-40, 1997), and there is no evidence of interaction between TRAF2 and TRAF3 (see, e.g., Wajant et al., Cytokine Growth Factor 10:15-26, 1999). Thus, TRAF3 is likely directly recruited to LTβR upon LIGHT treatment. In contrast, the recruitment of cIAP1 to LTβR probably occurs via its interaction with TRAF2 because cIAP1-TRAF2 interaction has been shown in vitro and there is no evidence of interaction between cIAP1 and receptor or TRAF3.

Interestingly, the cIAP1 in the complex recognized by a polyclonal antibody raised against the C-terminus of cIAP1 (R&D systems, AF818) is about 60 kDa, which is smaller than the full-length cIAP1 (about 70 kDa) in cell lysate. This 60 kDa band was not detected by another antibody raised against a peptide at the BIR1 domain of the cIAP1 (sc-1867, Santa Cruz, which recognizes 70 kDa-cIAP1 in cell lysate). These observations indicate that the N-terminus of cIAP1 in the complex is cleaved.

Although two peptides from Smac in the LIGHT-LTβR complex were detected by mass spectrometry, an endogenous association was not detected using Smac antibodies (Alexis Biochemicals or Cell Signaling Technology). This result could be due to the low sensitivity of Smac antibodies. Therefore, the association of Smac with LTβR was investigated by overexpression in HEK293 cells that do not have endogenous LTβR and HVEM (Zhai et al., Clin. Invest. 102:1142-51, 1998). Smac was expressed as a C-terminal HA-tagged fusion protein and appeared as a doublet of 28 kDa and 23 kDa on the Western blot. These sizes corresponded to full length Smac with the N-terminal mitochondrial localization signal peptide (amino acid 1-55) and the mature Smac without its signal peptide (Du et al., Cell 102:33-42, 2000). Both forms were co-immunoprecipitated with Flag-tagged LTβR. When cytosol and mitochondria were fractioned, all the full length Smac was found to reside in the mitochondria fraction, and a significant amount (about one third) of the mature Smac was in the cytosolic fraction. Therefore, these data suggest that the cytosolic mature form of Smac is the physiological form of Smac that interacts with LTβR. The observation that the full-length Smac was co-immunoprecipitated with LTβR may be artificial, due to the disruption of the mitochondrial membrane by Triton X-100.

There was no further increase of Smac recruitment when stimulated with LIGHT (data not shown). This is likely due to the aggregation and activation of LTβR resulting from over-expression. In the reciprocal immunoprecipitation of Smac using HA antibody, LTβR was detected, which further confirms the association. In accordance with the observation in U937 cells (discussed above), endogenous TRAF2, cIAP1

(60 kDa) and TRAF3 were also found to be recruited to LTβR overexpressed in HEK 293 cells. Furthermore, endogenous TRAF2 and cIAP1 were detected in the reciprocal immunoprecipitation of Smac, indicating the formation of a complex of LTβR-TRAF2-cIAP1-Smac. Taken together, these data strongly support the physiological association of TRAF2, TRAF3, cIAP1, and Smac with LTβR.

In contrast to the full-length Smac, the deletion mutant of Smac (Δ76Smac) that lacks both the cIAP1 binding site (amino acid 56-75) and mitochondrial localization signal lost the ability to bind to LTβR. This suggests that the cIAP1 binding site of Smac is important for its recruitment to the receptor. The interaction between the N-terminus of Smac and the BIR3 domain of XIAP has been demonstrated by the X-ray crystal structure and mutational analysis (Chai et al., Nature 406:855-862, 2000; Wu et al., Nature 408:1008-12, 2000). Because known IAP polypeptides are highly homologous it is likely that the recruitment of Smac is mediated by its interaction with the BIR3 domain of cIAP1. Despite the difference between the full-length and the deletion mutant of Smac, the level of cIAP1, TRAF2, and TRAF3 on LTβR remained the same, suggesting that the recruitment of Smac occurs after the recruitment of TRAF2, TRAF3 and cIAP1.

EXAMPLE 3

Smac Potentiates LTβR-induced Apoptosis

Smac has been shown to promote apoptosis in response to several stimuli, such as UV irradiation, that trigger the mitochondria-mediated apoptosis pathway (Du et al., Cell 102:33-42, 2000). MCF7 cells were cotransfected with plasmids expressing β-galactosidase (pEMC-βgal) and Smac-HA, Δ76 Smac-HA or empty vector. After 24 hours, cells were treated with PBS, LIGHT (20 ng/ml), or LTα1β2 (20 ng/ml), respectively, for 6 hours, then fixed, and stained with X-gal. Apoptosis was assessed by the morphological analysis of the βgal-expressing cells. (see Example 1 for details).

Figure 2:
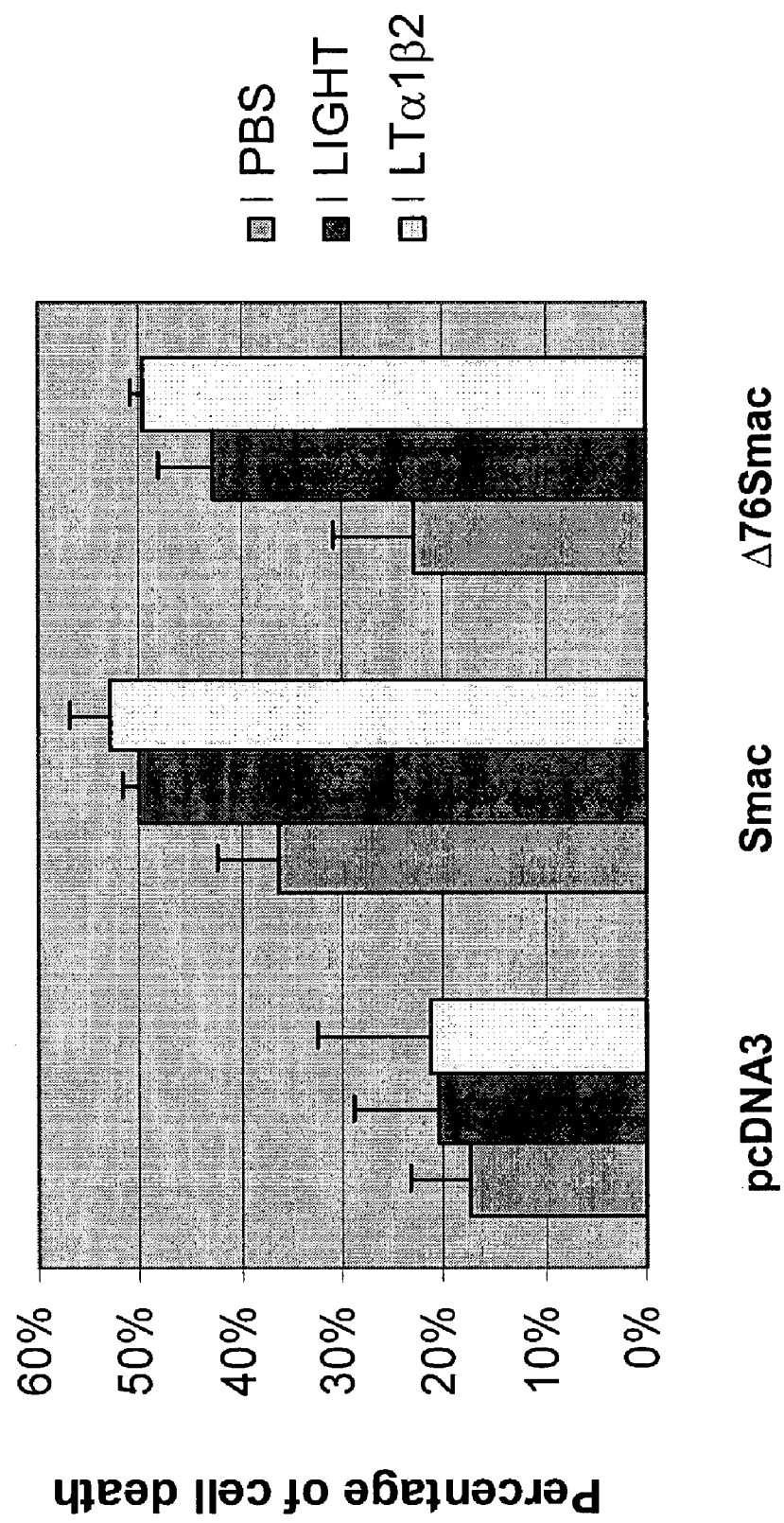
FIG. 2 is a histogram showing the effect of Smac and Δ76 Smac on LIGHT-induced apoptosis.

The results are shown in FIG. 2. Apoptosis was assessed by morphological analysis and expressed as a percentage of apoptotic cells (round and detached) in total transfected blue cells. Bars represent the average of duplicate samples in three separate experiments. In each experiment, more than 1000 cells were counted.

Overexpression of full-length Smac potentiated apoptosis in MCF7 cells, and stimulation of LIGHT further increased apoptosis. A similar effect was observed in the LTα1β2-stimulated cells. Interestingly, mutant Δ76 Smac, which lost the ability to recruit to the receptor, could still potentiate LTβR-mediated apoptosis to a degree similar to the full-length Smac. This result suggests that C-terminus of Smac also possesses proapoptotic activity and is independent of its interaction with cIAP1.

Figure 3:
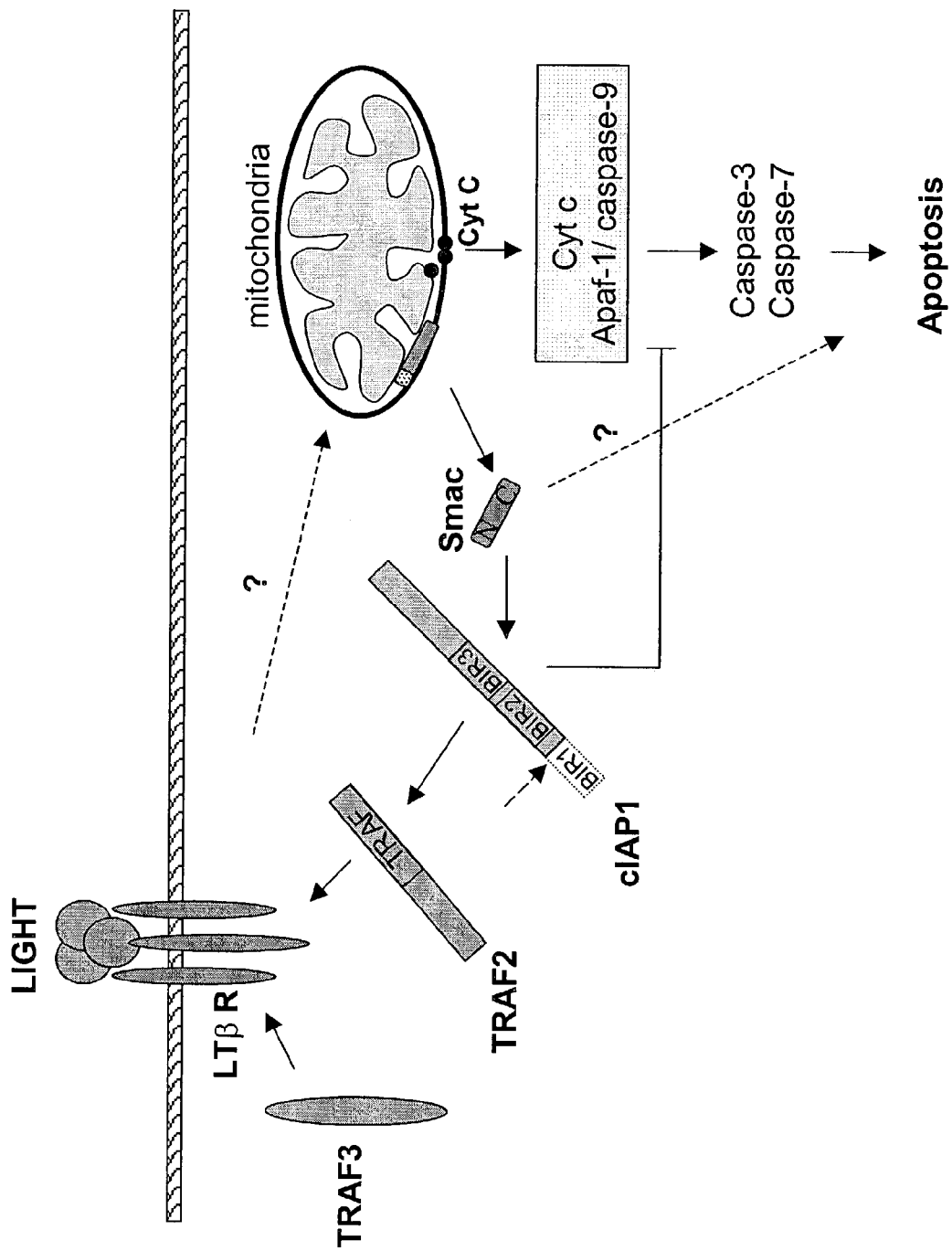
FIG. 3 is a model of LTβR-mediated apoptosis.

While not wishing to be bound by theory, a model for LTβR-induced apoptosis is diagrammed in FIG. 3. Upon binding of LIGHT to LTβR, TRAF2 is first recruited to the receptor, followed by TRAF3 and cIAP1, during which the BIR1 domain of cIAP1 is cleaved. The cIAP1 on the receptor inhibits apoptosis by direct interaction with caspases. The initial LIGHT-LTβR complex also triggers the mitochondria-mediated apoptosis pathway, by an unknown mechanism, which induces the release of Smac from mitochondria. Cytosolic Smac, which lacks the N-terminal mitochondrial localization signal, is then recruited to the receptor via its interaction with cIAP1. The interaction of N-terminus of Smac with cIAP1 releases the inhibition of cIAP1 on caspases while the C-terminus of Smac works in concert with N-terminus to promote apoptosis by yet to be identified mechanism. It has been reported that LTβR-induced apoptosis requires the addition of IFNγ (Browning et al., J. Exp. Med. 183:867-78, 1996). Consistent with the proposed role of Smac in this model, IFNγ has shown to induce de novo synthesis of Smac in WEHI 279 cells (Yoshikawa et 1., 167:2487-95, 2001). It is possible that TRAF3 promotes the cIAP1-Smac pathway by triggering the release of Smac from mitochondria.

The descriptions given are intended to exemplify, but not limit, the scope of the invention.

What is claimed is:

1. A method of identifying a modulator of a lymphotoxin beta receptor (LTβR) complex signaling pathway, the method comprising
   contacting a cell expressing an LTβR polypeptide with a test agent;
   determining whether the test agent modulates activity or expression of a Smac polypeptide in said cell; and
   further determining whether a test agent that modulates activity or expression of a Smac polypeptide directly interferes with LTβR-ligand binding,
   wherein interference with LTβR-ligand binding identifies said test agent as a modulator of a lymphotoxin beta receptor (LTβR) complex signaling pathway.

2. The method of claim 1, further comprising determining whether the test agent modulates mitochondrial-mediated apoptosis in said cell.

3. The method of claim 1, wherein said LTβR ligand is a LIGHT polypeptide complex.

4. The method of claim 1, wherein said LTβR ligand is a Ltα1f32 polypeptide complex.

5. The method of claim 1, wherein said LTβR complex comprises LTβR, TRAF3, TRAF2, cIAP1, and Smac polypeptides.

6. The method of claim 1, wherein said modulation is inhibition of the LTβR complex signaling pathway.

7. The method of claim 1, wherein said modulation is enhancement of the LTβR complex signaling pathway.

8. A method of identifying a modulator of a lymphotoxin beta receptor (LTβR) complex signaling pathway, the method comprising
   contacting a cell expressing an LTβR with a test agent;
   determining whether the test agent modulates activity or expression of a cIAP1 polypeptide in said cell; and
   further determining whether a test agent that modulates activity or expression of a cIAP1 polypeptide directly interferes with LTβR-ligand binding,
   wherein interference with LTβR-ligand binding identifies said test agent as a modulator of a lymphotoxin beta receptor (LTβR) complex signaling pathway.

9. The method of claim 8, further comprising determining whether the test agent modulates mitochondrial-mediated apoptosis in said cell.

10. The method of claim 8 wherein said LTβR ligand is a LIGHT polypeptide complex.

11. The method of claim 8 wherein said LTβR ligand is a Ltα1β2 polypeptide complex.

12. The method of claim 8, wherein said LTβR complex comprises LTβR, TRAF3, TRAF2, cIAP1, and Smac polypeptides.

13. The method of claim 8, wherein said modulation is inhibition of the LTβR complex signaling pathway.

14. The method of claim 8, wherein said modulation is enhancement of the LTβR complex signaling pathway.

15. A method of identifying a modulator of a lymphotoxin beta receptor (LTβR) complex signaling pathway, the method comprising
    contacting a cell expressing an LTβR with a test agent;
    determining whether the test agent modulates activity or expression of a TRAF2 polypeptide in said cell; and
    further determining whether a test agent that modulates activity or expression of a TRAF2 polypeptide directly interferes with LTβR-ligand binding,
    wherein interference with LTβR-ligand binding identifies said test agent as a modulator of a lymphotoxin beta receptor (LTβR) complex signaling pathway.

16. The method of claim 15, further comprising determining whether the test agent modulates mitochondrial-mediated apoptosis in said cell.

17. The method of claim 15, wherein said LTβR ligand is a LIGHT polypeptide complex.

18. The method of claim 15, wherein said LTβR ligand is a Ltα1β2 polypeptide complex.

19. The method of claim 15, wherein said LTβR complex comprises LTβR, TRAF3, TRAF2, cIAP1, and Smac polypeptides.

20. The method of claim 15, wherein said modulation is inhibition of the LTβR complex signaling pathway.

21. A method of identifying a modulator of a lymphotoxin beta receptor (LTβR) complex signaling pathway, the method comprising
    contacting a cell expressing an LTβR polypeptide with a test agent;
    determining whether the test agent modulates activity or expression of an ERH polypeptide in said cell; and
    further determining whether a test agent that modulates activity or expression of an ERH polypeptide modulates LTβR-ligand binding,
    wherein interference with LTβR-ligand binding identifies said test agent as a modulator a modulator of a lymphotoxin beta receptor (LTβR) complex signaling pathway.

22. The method of claim 21, further comprising determining whether the test agent modulates mitochondrial-mediated apoptosis in said cell.

23. The method of claim 21, wherein said LTβR ligand is a LIGHT polypeptide complex.

24. The method of claim 21, wherein said LTβR ligand is a Ltα1β2 polypeptide complex.

25. The method of claim 21, wherein said LTβR complex comprises LTβR, TRAF3, TRAF2, cIAP1, and Smac polypeptides.

26. The method of claim 21, wherein said modulation is inhibition of the LTβR complex signaling pathway.

27. The method of claim 21, wherein said modulation is enhancement of the LTβR complex signaling pathway.

* * * * *

SEQUENCE LISTING

```
<160> NUMBER OF SEQ ID NOS: 35

<210> SEQ ID NO 1
<211> LENGTH: 501
<212> TYPE: PRT
<213> ORGANISM: Homo sapiens

<400> SEQUENCE: 1

Met Ala Ala Ser Val Thr Pro Pro Gly Ser Leu Glu Leu Leu Gln
  1               5                  10                  15

Pro Gly Phe Ser Lys Thr Leu Leu Gly Thr Lys Leu Glu Ala Lys Tyr
                 20                  25                  30

Leu Cys Ser Ala Cys Arg Asn Val Leu Arg Arg Pro Phe Gln Ala Gln
         35                  40                  45

Cys Gly His Arg Tyr Cys Ser Phe Cys Leu Ala Ser Ile Leu Ser Ser
     50                  55                  60

Gly Pro Gln Asn Cys Ala Ala Cys Val His Glu Gly Ile Tyr Glu Glu
 65                  70                  75                  80
```

-continued

```
Gly Ile Ser Ile Leu Glu Ser Ser Ala Phe Pro Asp Asn Ala Ala
                 85                  90                  95

Arg Arg Glu Val Glu Ser Leu Pro Ala Val Cys Pro Ser Asp Gly Cys
                100                 105                 110

Thr Trp Lys Gly Thr Leu Lys Glu Tyr Glu Ser Cys His Glu Gly Arg
            115                 120                 125

Cys Pro Leu Met Leu Thr Glu Cys Pro Ala Cys Lys Gly Leu Val Arg
            130                 135                 140

Leu Gly Glu Lys Glu Arg His Leu Glu His Glu Cys Pro Glu Arg Ser
145                 150                 155                 160

Leu Ser Cys Arg His Cys Arg Ala Pro Cys Cys Gly Ala Asp Val Lys
                165                 170                 175

Ala His His Glu Val Cys Pro Lys Phe Pro Leu Thr Cys Asp Gly Cys
                180                 185                 190

Gly Lys Lys Lys Ile Pro Arg Glu Lys Phe Gln Asp His Val Lys Thr
            195                 200                 205

Cys Gly Lys Cys Arg Val Pro Cys Arg Phe His Ala Ile Gly Cys Leu
            210                 215                 220

Glu Thr Val Glu Gly Lys Gln Gln Glu His Glu Val Gln Trp Leu
225                 230                 235                 240

Arg Glu His Leu Ala Met Leu Leu Ser Ser Val Leu Glu Ala Lys Pro
                245                 250                 255

Leu Leu Gly Asp Gln Ser His Ala Gly Ser Glu Leu Leu Gln Arg Cys
            260                 265                 270

Glu Ser Leu Glu Lys Lys Thr Ala Thr Phe Glu Asn Ile Val Cys Val
            275                 280                 285

Leu Asn Arg Glu Val Glu Arg Val Ala Met Thr Ala Glu Ala Cys Ser
290                 295                 300

Arg Gln His Arg Leu Asp Gln Asp Lys Ile Glu Ala Leu Ser Ser Lys
305                 310                 315                 320

Val Gln Gln Leu Glu Arg Ser Ile Gly Leu Lys Asp Leu Ala Met Ala
                325                 330                 335

Asp Leu Glu Gln Lys Val Arg Pro Phe Gln Ala Gln Cys Gly His Arg
            340                 345                 350

Tyr Cys Ser Phe Cys Leu Ala Ser Ile Leu Arg Lys Leu Gln Glu Ala
            355                 360                 365

Val Ala Gly Arg Ile Pro Ala Ile Phe Ser Pro Ala Phe Tyr Thr Ser
370                 375                 380

Arg Tyr Gly Tyr Lys Met Cys Leu Arg Ile Tyr Leu Asn Gly Asp Gly
385                 390                 395                 400

Thr Gly Arg Gly Thr His Leu Ser Leu Phe Phe Val Val Met Lys Gly
                405                 410                 415

Pro Asn Asp Ala Leu Leu Arg Trp Pro Phe Asn Gln Lys Val Thr Leu
            420                 425                 430

Met Leu Leu Asp Gln Asn Asn Arg Glu His Val Ile Asp Ala Phe Arg
            435                 440                 445

Pro Asp Val Thr Ser Ser Ser Phe Gln Arg Pro Val Asn Asp Met Asn
            450                 455                 460

Ile Ala Ser Gly Cys Pro Leu Phe Cys Pro Val Ser Lys Met Glu Ala
465                 470                 475                 480

Lys Asn Ser Tyr Val Arg Asp Asp Ala Ile Phe Ile Lys Ala Ile Val
                485                 490                 495

Asp Leu Thr Gly Leu
```

```
<210> SEQ ID NO 2
<211> LENGTH: 1506
<212> TYPE: DNA
<213> ORGANISM: Homo sapiens

<400> SEQUENCE: 2
atggctgcag ctagcgtgac ccccctggc tccctggagt tgctacagcc cggcttctcc      60
aagaccctcc tggggaccaa gctggaagcc aagtacctgt gctccgcctg cagaaacgtc     120
ctccgcaggc ccttccaggc gcagtgtggc accggtact gctccttctg cctggccagc      180
atcctcagct ctgggcctca gaactgtgct gcctgtgttc acgagggcat atatgaagaa     240
ggcatttcta ttttagaaag cagttcggcc ttcccagata tgctgcccg cagggaggtg      300 gagagcctgc cggccgtctg tcccagtgat ggatgcacct ggaaggggac cctgaaagaa     360
tacgagagct gccacgaagg ccgctgcccg ctcatgctga ccgaatgtcc cgcgtgtaaa     420
ggcctggtcc gccttggtga aaaggagcgc cacctggagc acgagtgccc ggagagaagc     480
ctgagctgcc ggcattgccg gcaccctgc tgcggagcag acgtgaaggc gcaccacgag      540 gtctgccca gttccccctt aacttgtgac ggctgcggca agaagaagat ccccgggag       600 aagtttcagg accacgtcaa gacttgtggc aagtgtcgag tcccttgcag attccacgcc     660
atcggctgcc tcgagacggt agagggtgag aaacagcagg agcacgaggt gcagtggctg     720
cgggagcacc tggccatgct actgagctcg gtgctggagg caaagccct cttgggagac      780 cagagccacg cggggtcaga gctcctgcag aggtgcgaga gcctggagaa aagacggcc     840 acttttgaga acattgtctg cgtcctgaac cgggaggtgg agagggtggc catgactgcc     900
gaggcctgca gccggcagca ccggctggac caagacaaga ttgaagccct gagtagcaag     960
gtgcagcagc tggagaggag cattggcctc aaggacctgg cgatggctga cttggagcag    1020
aaggtcaggc ccttccaggc gcagtgtggc accggtact gctccttctg cctggccagc     1080
atcctcagga agctccagga agctgtggct ggccgcatac ccgccatctt ctccccagcc    1140
ttctacacca gcaggtacgg ctacaagatg tgtctgcgta tctacctgaa cggcgacggc    1200
accgggcgag gaacacacct gtccctcttc tttgtggtga tgaagggccc gaatgacgcc    1260
ctgctgcggt ggcccttcaa ccagaaggtg accttaatgc tgctcgacca gaataaccgg    1320
gagcacgtga ttgacgcctt caggcccgac gtgacttcat cctcttttca gaggccagtc    1380
aacgacatga acatcgcaag cggctgcccc ctcttctgcc ccgtctccaa gatggaggca    1440
aagaattcct acgtgcggga cgatgccatc ttcatcaagg ccattgtgga cctgacaggg    1500
ctctaa                                                                1506

<210> SEQ ID NO 3
<211> LENGTH: 618
<212> TYPE: PRT
<213> ORGANISM: Homo sapiens

<400> SEQUENCE: 3
```

Met His Lys Thr Ala Ser Gln Arg Leu Phe Pro Gly Pro Ser Tyr Gln
 1               5                  10                  15

Asn Ile Lys Ser Ile Met Glu Asp Ser Thr Ile Leu Ser Asp Trp Thr
                20                  25                  30

Asn Ser Asn Lys Gln Lys Met Lys Tyr Asp Phe Ser Cys Glu Leu Tyr
            35                  40                  45

-continued

```
Arg Met Ser Thr Tyr Ser Thr Phe Pro Ala Gly Val Pro Val Ser Glu
     50              55                  60

Arg Ser Leu Ala Arg Ala Gly Phe Tyr Tyr Thr Gly Val Asn Asp Lys
 65              70                  75                  80

Val Lys Cys Phe Cys Cys Gly Leu Met Leu Asp Asn Trp Lys Leu Gly
                 85                  90                  95

Asp Ser Pro Ile Gln Lys His Lys Gln Leu Tyr Pro Ser Cys Ser Phe
                100             105                 110

Ile Gln Asn Leu Val Ser Ala Ser Leu Gly Ser Thr Ser Lys Asn Thr
            115                 120             125

Ser Pro Met Arg Asn Ser Phe Ala His Ser Leu Ser Pro Thr Leu Glu
    130                 135             140

His Ser Ser Leu Phe Ser Gly Ser Tyr Ser Ser Leu Ser Pro Asn Pro
145             150                 155                 160

Leu Asn Ser Arg Ala Val Glu Asp Ile Ser Ser Ser Arg Thr Asn Pro
                165                 170             175

Tyr Ser Tyr Ala Met Ser Thr Glu Glu Ala Arg Phe Leu Thr Tyr His
                180             185                 190

Met Trp Pro Leu Thr Phe Leu Ser Pro Ser Glu Leu Ala Arg Ala Gly
            195                 200             205

Phe Tyr Tyr Ile Gly Pro Gly Asp Arg Val Ala Cys Phe Ala Cys Gly
    210             215                 220

Gly Lys Leu Ser Asn Trp Glu Pro Lys Asp Asp Ala Met Ser Glu His
225             230                 235                 240

Arg Arg His Phe Pro Asn Cys Pro Phe Leu Glu Asn Ser Leu Glu Thr
                245                 250             255

Leu Arg Phe Ser Ile Ser Asn Leu Ser Met Gln Thr His Ala Ala Arg
            260                 265             270

Met Arg Thr Phe Met Tyr Trp Pro Ser Ser Val Pro Val Gln Pro Glu
        275                 280             285

Gln Leu Ala Ser Ala Gly Phe Tyr Tyr Val Gly Arg Asn Asp Asp Val
    290                 295             300

Lys Cys Phe Cys Cys Asp Gly Gly Leu Arg Cys Trp Glu Ser Gly Asp
305                 310             315                 320

Asp Pro Trp Val Glu His Ala Lys Trp Phe Pro Arg Cys Glu Phe Leu
                325             330                 335

Ile Arg Met Lys Gly Gln Glu Phe Val Asp Glu Ile Gln Gly Arg Tyr
            340                 345             350

Pro His Leu Leu Glu Gln Leu Leu Ser Thr Ser Asp Thr Thr Gly Glu
        355                 360             365

Glu Asn Ala Asp Pro Pro Ile Ile His Phe Gly Pro Gly Glu Ser Ser
    370                 375             380

Ser Glu Asp Ala Val Met Met Asn Thr Pro Val Val Lys Ser Ala Leu
385             390                 395                 400

Glu Met Gly Phe Asn Arg Asp Leu Val Lys Gln Thr Val Gln Ser Lys
                405             410                 415

Ile Leu Thr Thr Gly Glu Asn Tyr Lys Thr Val Asn Asp Ile Val Ser
            420                 425             430

Ala Leu Leu Asn Ala Glu Asp Glu Lys Arg Glu Glu Lys Glu Lys
                435             440                 445

Gln Ala Glu Glu Met Ala Ser Asp Asp Leu Ser Leu Ile Arg Lys Asn
    450                 455             460

Arg Met Ala Leu Phe Gln Gln Leu Thr Cys Val Leu Pro Ile Leu Asp
```

```
                    465                 470                 475                 480

Asn Leu Leu Lys Ala Asn Val Ile Asn Lys Gln Glu His Asp Ile Ile
                485                 490                 495

Lys Gln Lys Thr Gln Ile Pro Leu Gln Ala Arg Glu Leu Ile Asp Thr
            500                 505                 510

Ile Leu Val Lys Gly Asn Ala Ala Asn Ile Phe Lys Asn Cys Leu
            515                 520                 525

Lys Glu Ile Asp Ser Thr Leu Tyr Lys Asn Leu Phe Val Asp Lys Asn
        530                 535                 540

Met Lys Tyr Ile Pro Thr Glu Asp Val Ser Gly Leu Ser Leu Glu Glu
545                 550                 555                 560

Gln Leu Arg Arg Leu Gln Glu Glu Arg Thr Cys Lys Val Cys Met Asp
                565                 570                 575

Lys Glu Val Ser Val Val Phe Ile Pro Cys Gly His Leu Val Val Cys
            580                 585                 590

Gln Glu Cys Ala Pro Ser Leu Arg Lys Cys Pro Ile Cys Arg Gly Ile
            595                 600                 605

Ile Lys Gly Thr Val Arg Thr Phe Leu Ser
        610                 615

<210> SEQ ID NO 4
<211> LENGTH: 239
<212> TYPE: PRT
<213> ORGANISM: Homo sapiens

<400> SEQUENCE: 4

Met Ala Ala Leu Lys Ser Trp Leu Ser Arg Ser Val Thr Ser Phe Phe
1               5                   10                  15

Arg Tyr Arg Gln Cys Leu Cys Val Pro Val Val Ala Asn Phe Lys Lys
                20                  25                  30

Arg Cys Phe Ser Glu Leu Ile Arg Pro Trp His Arg Thr Val Thr Ile
            35                  40                  45

Gly Phe Gly Val Thr Leu Cys Ala Val Pro Ile Ala Gln Lys Ser Glu
        50                  55                  60

Pro His Ser Leu Ser Ser Glu Ala Leu Met Arg Arg Ala Val Ser Leu
65                  70                  75                  80

Val Thr Asp Ser Thr Ser Thr Phe Leu Ser Gln Thr Thr Tyr Ala Leu
                85                  90                  95

Ile Glu Ala Ile Thr Glu Tyr Thr Lys Ala Val Tyr Thr Leu Thr Ser
            100                 105                 110

Leu Tyr Arg Gln Tyr Thr Ser Leu Leu Gly Lys Met Asn Ser Glu Glu
        115                 120                 125

Glu Asp Glu Val Trp Gln Val Ile Ile Gly Ala Arg Ala Glu Met Thr
    130                 135                 140

Ser Lys His Gln Glu Tyr Leu Lys Leu Glu Thr Thr Trp Met Thr Ala
145                 150                 155                 160

Val Gly Leu Ser Glu Met Ala Ala Glu Ala Tyr Gln Thr Gly Ala
                165                 170                 175

Asp Gln Ala Ser Ile Thr Ala Arg Asn His Ile Gln Leu Val Lys Leu
            180                 185                 190

Gln Val Glu Glu Val His Gln Leu Ser Arg Lys Ala Gly Thr Lys Leu
        195                 200                 205

Ala Glu Ala Gln Ile Glu Glu Leu Arg Gln Lys Thr Gln Glu Glu Gly
    210                 215                 220
```

Glu Arg Ala Glu Ser Glu Gln Glu Ala Tyr Leu Arg Glu Asp
225                 230                 235

<210> SEQ ID NO 5
<211> LENGTH: 720
<212> TYPE: DNA
<213> ORGANISM: Homo sapiens

<400> SEQUENCE: 5
atggcggctc tgaagagttg gctgtcgcgc agcgtaactt cattcttcag gtacagacag    60
tgtttgtgtg ttcctgttgt ggctaacttt aagaagcggt gtttctcaga attgataaga   120
ccatggcaca gaactgtgac gattggcttt ggagtaaccc tgtgtgcggt tcctattgca   180
cagaaatcag agcctcattc ccttagtagt gaagcattga tgaggagagc agtgtctttg   240
gtaacagata gcacctctac ctttctctct cagaccacat atgcgttgat tgaagctatt   300
actgaatata ctaaggctgt ttatacctta acttctcttt accgacaata tacaagttta   360
cttgggaaaa tgaattcaga ggaggaagat gaagtgtggc aggtgatcat aggagccaga   420
gctgagatga cttcaaaaca ccaagagtac ttgaagctgg aaaccacttg gatgactgca   480
gttggtcttt cagagatggc agcagaagct gcatatcaaa ctggcgcaga tcaggcctct   540
ataaccgcca ggaatcacat tcagctggtg aaactgcagg tggaagaggt gcaccagctc   600
tcccggaaag cagaaaccaa gctggcagaa gcacagatag aagagctccg tcagaaaaca   660
caggaggaag gggaggagcg ggctgagtcg gagcaggagg cctacctgcg tgaggattga   720

<210> SEQ ID NO 6
<211> LENGTH: 104
<212> TYPE: PRT
<213> ORGANISM: Homo sapiens

<400> SEQUENCE: 6

Met Ser His Thr Ile Leu Leu Val Gln Pro Thr Lys Arg Pro Glu Gly
1               5                   10                  15

Arg Thr Tyr Ala Asp Tyr Glu Ser Val Asn Glu Cys Met Glu Gly Val
                20                  25                  30

Cys Lys Met Tyr Glu Glu His Leu Lys Arg Met Asn Pro Asn Ser Pro
            35                  40                  45

Ser Ile Thr Tyr Asp Ile Ser Gln Leu Phe Asp Phe Ile Asp Asp Leu
        50                  55                  60

Ala Asp Leu Ser Cys Leu Val Tyr Arg Ala Asp Thr Gln Thr Tyr Gln
65                  70                  75                  80

Pro Tyr Asn Lys Asp Trp Ile Lys Glu Lys Ile Tyr Val Leu Leu Arg
                85                  90                  95

Arg Gln Ala Gln Gln Ala Gly Lys
            100

<210> SEQ ID NO 7
<211> LENGTH: 315
<212> TYPE: DNA
<213> ORGANISM: Homo sapiens

<400> SEQUENCE: 7
atgtctcaca ccattttgct ggtacagcct accaagaggc cagaaggcag aacttatgct    60
gactacgaat ctgtgaatga atgcatggaa ggtgtttgta aaatgtatga agaacatctg   120
aaaagaatga atcccaacag tccctctatc acatatgaca tcagtcagtt gtttgatttc   180
atcgatgatc tggcagacct cagctgcctg gtttaccgag ctgatacccag acataccag   240

```
ccttataaca aagactggat taaagagaag atctacgtgc tccttcgtcg gcaggcccaa    300
caggctggga aataa                                                    315
```

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Fragment of
      LIGHT Protein

<400> SEQUENCE: 8

Ser Tyr His Asp Gly Ala Leu Val Val Thr Lys
 1               5                  10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Fragment of
      LTBetaR Protein

<400> SEQUENCE: 9

Glu Tyr Tyr Glu Pro Gln His Arg
 1               5

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Fragment of
      LTBetaR Protein

<400> SEQUENCE: 10

Asp Gln Glu Lys Glu Tyr Tyr Glu Pro Gln His Arg
 1               5                  10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Fragment of
      LTBetaR Protein

<400> SEQUENCE: 11

Asn Gln Phe Ile Thr His Asp
 1               5

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Fragment of
      TRAF3 protein

<400> SEQUENCE: 12

Tyr Gly Cys Val Phe Gln Gly Thr Asn Gln Gln Ile Lys
 1               5                  10

<210> SEQ ID NO 13
<211> LENGTH: 11
<212> TYPE: PRT

<213> ORGANISM: Artificial Sequence
<220> FEATURE:
<223> OTHER INFORMATION: Description of Artificial Sequence: Fragment of
     TRAF3 protein.

<400> SEQUENCE: 13

Asn Thr Gly Leu Leu Glu Ser Gln Leu Ser Arg
  1               5                  10

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Fragment of
     TRAF3 protein.

<400> SEQUENCE: 14

Thr Leu Ser Leu Tyr Ser Gln Pro Phe Tyr Thr Gly Tyr Phe Gly Tyr
  1               5                  10                  15

Lys

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Fragment of
     TRAF2 protein.

<400> SEQUENCE: 15

Tyr Leu Cys Ser Ala Cys Arg
  1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Fragment of
     TRAF2 protein.

<400> SEQUENCE: 16

Arg Pro Phe Gln Ala Gln Cys Gly His Arg
  1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Fragment of
     TRAF2 protein.

<400> SEQUENCE: 17

Cys Pro Leu Met Leu Thr Glu Cys Pro Ala Cys Lys
  1               5                  10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Fragment of
     TRAF2 protein.

<400> SEQUENCE: 18

```
Phe Pro Leu Thr Cys Asp Gly Cys Gly Lys Lys
  1               5                  10
```

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Fragment of
      TRAF2 protein.

<400> SEQUENCE: 19

```
Phe His Ala Ile Gly Cys Leu Glu Thr Val Glu Gly Glu Lys
  1               5                  10
```

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Fragment of
      TRAF2 protein.

<400> SEQUENCE: 20

```
Val Ala Met Thr Ala Glu Ala Cys Ser Arg
  1               5                  10
```

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Fragment of
      TRAF2 protein.

<400> SEQUENCE: 21

```
Val Gln Gln Leu Glu Arg
  1               5
```

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Fragment of
      TRAF2 protein.

<400> SEQUENCE: 22

```
Asp Leu Ala Met Ala Asp Leu Glu Gln Lys
  1               5                  10
```

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Fragment of
      TRAF2 protein.

<400> SEQUENCE: 23

```
Arg Pro Phe Gln Ala Gln Cys Gly His Arg
  1               5                  10
```

<210> SEQ ID NO 24
<211> LENGTH: 13
<212> TYPE: PRT
<213> ORGANISM: Artificial Sequence
<220> FEATURE:

```
<223> OTHER INFORMATION: Description of Artificial Sequence: Fragment of
      TRAF2 protein.

<400> SEQUENCE: 24

Ile Pro Ala Ile Phe Ser Pro Ala Phe Tyr Thr Ser Arg
 1               5                  10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Fragment of
      TRAF2 protein.

<400> SEQUENCE: 25

Ile Tyr Leu Asn Gly Asp Gly Thr Gly Arg
 1               5                  10

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Fragment of
      TRAF2 protein.

<400> SEQUENCE: 26

Trp Pro Phe Asn Gln Lys
 1               5

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Fragment of
      TRAF2 protein.

<400> SEQUENCE: 27

Asn Ser Tyr Val Arg Asp Asp Ala Ile Phe Ile Lys
 1               5                  10

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Fragment of
      cIAP1 protein.

<400> SEQUENCE: 28

Ala Val Glu Asp Ile Ser Ser Ser Arg
 1               5

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Fragment of
      cIAP1 protein.

<400> SEQUENCE: 29

Ala Gly Phe Tyr Tyr Ile Gly Pro Gly Asp Arg
 1               5                  10
```

```
<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Fragment of
      cIAP1 protein.

<400> SEQUENCE: 30

Val Ala Cys Phe Ala Cys Gly Gly Lys
  1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Fragment of
      cIAP1 protein.

<400> SEQUENCE: 31

Ser Ala Leu Glu Met Gly Phe Asn Arg
  1               5

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Fragment of
      Smac protein.

<400> SEQUENCE: 32

Ala Val Tyr Thr Leu Thr Ser Leu Tyr Arg
  1               5                  10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Fragment of
      Smac protein.

<400> SEQUENCE: 33

Leu Ala Glu Ala Gln Ile Glu Glu Leu Arg
  1               5                  10

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Fragment of
      LIGHT protein.

<400> SEQUENCE: 34

Ala Gly Tyr Tyr Tyr Ile Tyr Ser Lys
  1               5

<210> SEQ ID NO 35
<211> LENGTH: 10
<212> TYPE: PRT
<213> ORGANISM: Artificial Sequence
```

-continued

```
<220> FEATURE:
<223> OTHER INFORMATION: Description of Artificial Sequence: Fragment of
      LIGHT protein.

<400> SEQUENCE: 35

Ala Ser Thr Ile Thr His Gly Leu Tyr Lys
 1               5                   10
```